United States Patent
Blomberg et al.

(10) Patent No.: US 9,488,608 B2
(45) Date of Patent: Nov. 8, 2016

(54) METHOD FOR DETERMINING THE DEW POINT OF A VAPORISED HYDROCARBON FEEDSTOCK

(71) Applicant: SHELL OIL COMPANY, Houston, TX (US)

(72) Inventors: Jan Blomberg, Amsterdam (NL); Pieter Huizenga, Amsterdam (NL); Muralikrishna Venkatacharyulu Khandavilli, Bangalor (IN); Walter Stanley Postula, Houston, TX (US)

(73) Assignee: Shell Oil Company, Houston, TX (US)

( * ) Notice: Subject to any disclaimer, the term of this patent is extended or adjusted under 35 U.S.C. 154(b) by 373 days.

(21) Appl. No.: 14/356,834

(22) PCT Filed: Nov. 13, 2012

(86) PCT No.: PCT/EP2012/072485
§ 371 (c)(1),
(2) Date: May 7, 2014

(87) PCT Pub. No.: WO2013/072307
PCT Pub. Date: May 23, 2013

(65) Prior Publication Data
US 2015/0063407 A1    Mar. 5, 2015

Related U.S. Application Data

(60) Provisional application No. 61/561,633, filed on Nov. 18, 2011.

(51) Int. Cl.
*G01N 25/68* (2006.01)
*G01N 25/66* (2006.01)
(Continued)

(52) U.S. Cl.
CPC .............. *G01N 25/66* (2013.01); *G01N 25/08* (2013.01); *G01N 33/225* (2013.01); *G01N 33/28* (2013.01)

(58) Field of Classification Search
CPC ....................................................... G01N 25/68
USPC ....................................................... 374/27–28
See application file for complete search history.

(56) References Cited

U.S. PATENT DOCUMENTS 3,589,169 A * 6/1971 Lafitte .................. G01N 25/142
                                                    23/294 R
3,651,686 A * 3/1972 Dizio ...................... G01N 25/14
                                                    23/294 R (Continued)

FOREIGN PATENT DOCUMENTS

CN          1701227        11/2005
CN          101990637      3/2011

(Continued)

*Primary Examiner* — Clayton E Laballe
*Assistant Examiner* — Leon W Rhodes, Jr.

(57) ABSTRACT

The invention provides a method for determining the dew point of a vaporized hydrocarbon feedstock, comprising heating a hydrocarbon feedstock and a hydrocarbon diluent to a first temperature and maintaining the feedstock and diluent at that temperature until all hydrocarbon feedstock is vaporized and a homogeneous mixture is obtained; passing a first flow of the mixture through a first zone maintained at a second temperature, which is lower than the first temperature; halting the first flow; passing a sweep gas through the first zone and providing the sweep gas to a detector for detecting hydrocarbons; decreasing the temperature of the first zone, wherein steps (c) to (f) are repeated at least until a hydrocarbon presence is detected in the sweep gas.
The invention further provides a method for measuring the dew point of a steam cracker feed and a system for determining the dew point of a vaporized hydrocarbon feedstock.

14 Claims, 1 Drawing Sheet

(51) Int. Cl.
  *G01N 33/22* (2006.01)
  *G01N 33/28* (2006.01)
  *G01N 25/08* (2006.01)

(56) References Cited

U.S. PATENT DOCUMENTS

| | | | | |
|---|---|---|---|---|
| 3,724,169 | A | * | 4/1973 | Santeler ............ G01N 25/14 95/289 |
| 4,214,473 | A | * | 7/1980 | Edwards, Jr. ........ G01N 25/142 374/25 |
| 4,589,274 | A | | 5/1986 | Boyle et al. |
| 5,492,555 | A | * | 2/1996 | Strunk ................ G01N 30/463 73/23.37 |
| 2007/0147467 | A1 | | 6/2007 | Arnold et al. |

FOREIGN PATENT DOCUMENTS

| | | |
|---|---|---|
| CN | 102128858 | 7/2011 |
| EP | 0141438 | 5/1985 |
| FR | 2710752 | 4/1995 |
| GB | 2282667 | 4/1995 |
| GB | 2417565 | 3/2006 |

* cited by examiner

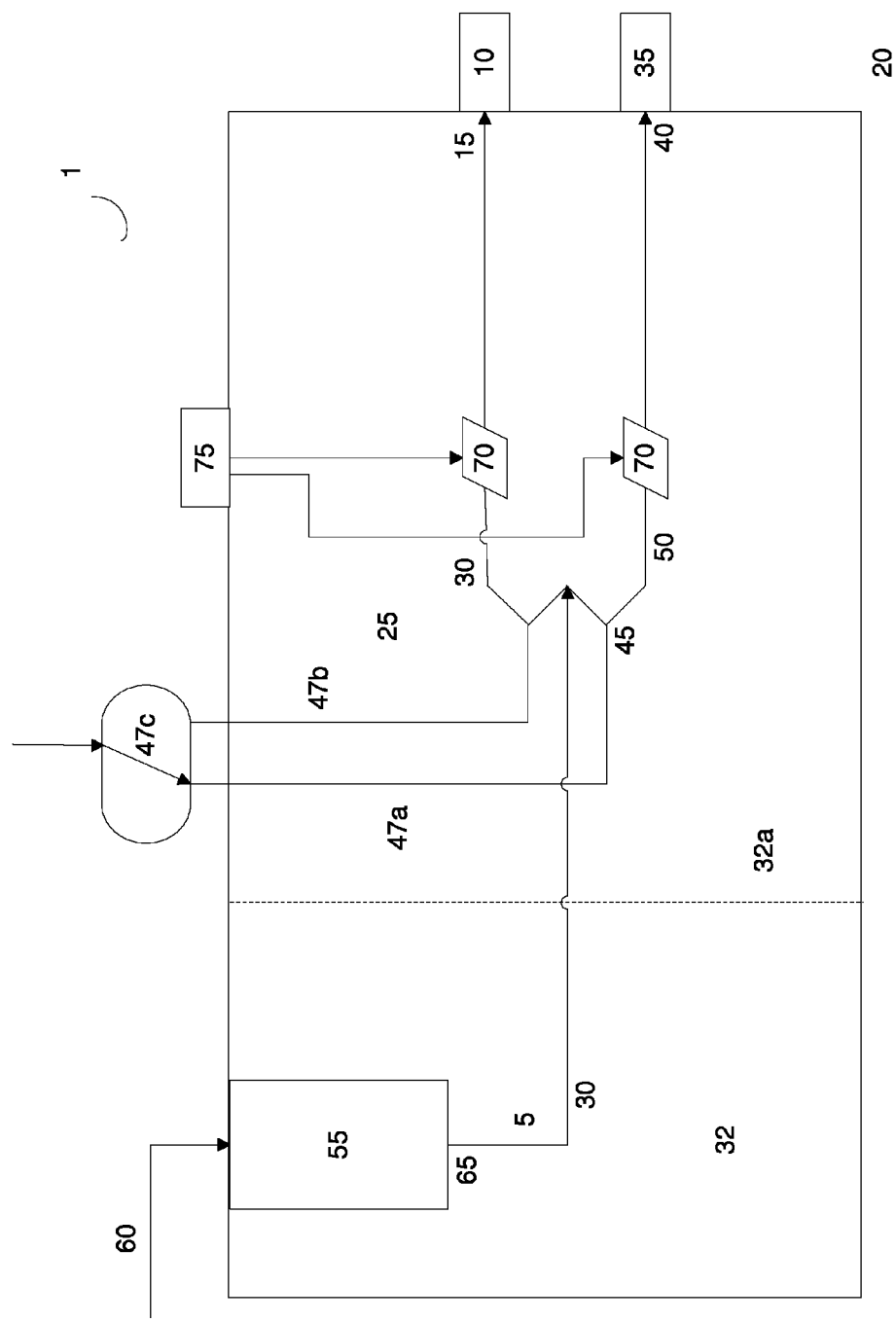

METHOD FOR DETERMINING THE DEW POINT OF A VAPORISED HYDROCARBON FEEDSTOCK

PRIORITY CLAIM

The present application is the National Stage (§371) of International Application No. PCT/EP2012/072485, filed 13 Nov. 2012, which claims priority from U.S. provisional No. 61/561,633, filed 18 Nov. 2011, the disclosures of which are incorporated herein by reference.

FIELD OF THE INVENTION

The invention relates to a method for determining the dew point of a vaporised hydrocarbon feedstock, a method for measuring the dew point of a steam cracker feed and a system for determining the dew point of a vaporised hydrocarbon feedstock.

BACKGROUND TO THE INVENTION

The hydrocarbon dew point of a vaporised hydrocarbon-comprising stream, i.e. the temperature at which the first hydrocarbons in the stream condense, is a key parameter in many industrial applications. Over time, such condensed hydrocarbons can cause equipment fouling, which in turn may lead to downtime for cleaning or even replacement of equipment.

In general, the hydrocarbon dew point dictates the minimum temperature required in a process to avoid undesired condensation. One example of such processes is the transmission of natural gas through pipelines, where the hydrocarbon dew point is sub-zero and the aim is to prevent condensation of C2 to C5 hydrocarbons. Another example is the gasification of biomass, where a tar by-product is formed having a dew point in the order of 170° C. In for instance steam cracking of naphtha, hydrowax, gasoline or gasoil type feedstocks, the feedstock is exposed to very high temperatures in specific parts of the convection section of the furnace. Any non-vaporised liquids contacting the walls of the pipes in this part of the convection section would result in an almost instantaneous decomposition and coke formation. Therefore, it is required to maintain the temperature of the mixture of steam and vaporised hydrocarbon feedstock in these sections above the dew point of the hydrocarbons in the feedstock. Due to the nature of the hydrocarbons in the steam cracker feedstock, the dew point may be above 170° C.

Commercially available apparatuses for measuring hydrocarbon dew point temperatures are based on detection of the dew by light reflection from a mirror. A hydrocarbon vapour at a set temperature is sent over a highly polished steel surface/mirror, the central point of which is maintained below the temperature of the vapour. The mirror is conical in shape, with the central point being physically and thermally the lowest point. Light is focused on this central point and as soon as hydrocarbons condense on the mirror, the reflection pattern of the light changes. The temperature of the central point of the mirror is reported as the dew point temperature.

These commercially available apparatuses can measure dew points up to a maximum of 170° C. owing to temperature limitations of the electronics and fiber optic cables.

For steam cracking feedstocks dew points are typically much greater than 170° C., ranging up to 500° C. Modifying the commercial apparatuses to meet this temperature requirement would likely be difficult; therefore there is a need in the art for a new method for determining the dew point of a vaporised hydrocarbon feedstock.

SUMMARY OF THE INVENTION

It has now been found that the dew point of a vaporised hydrocarbon feedstock can be determined by a condensation/re-vaporisation method using a standard hydrocarbon detector to detect condensation.

Accordingly, the present invention provides a method for determining the dew point of a vaporised hydrocarbon feedstock, comprising a) providing a hydrocarbon feedstock and a non-hydrocarbonaceous diluent;

b) heating the hydrocarbon feedstock and diluent to a first temperature and maintaining the hydrocarbon feedstock and diluent at the first temperature until all hydrocarbon feedstock is vaporized and a homogeneous mixture of the hydrocarbon feedstock and diluent is obtained;

c) passing a first flow of the mixture through a first zone maintained at a second temperature, which is lower than the first temperature;

d) halting the first flow;

e) passing a second flow comprising a non-hydrocarbonaceous sweep gas through the first zone and providing the sweep gas exiting the first zone to a detector suitable for detecting the presence of hydrocarbons;

f) decreasing the temperature of the first zone, wherein steps (c) to (f) are repeated at least until a hydrocarbon presence is detected in the sweep gas.

The present invention allows for the determination of the hydrocarbon dew point of the vaporised hydrocarbon feedstock at a variable extent of dilution.

The method utilizes standard hydrocarbon detection devices, which are readily available and can be used also at higher temperatures without the need for modifications.

In a further aspect, the invention provides a method for measuring the dew point of a steam cracker feed comprising steam and a hydrocarbon feedstock at a steam to hydrocarbon feedstock weight ratio, comprising providing an amount of the hydrocarbon feedstock and an amount of non-hydrocarbonaceous diluent other than steam; and determining the dew point of the vaporised hydrocarbon feedstock with a method according to any one of claims 1 to 9, wherein the amount of diluent provided is equimolar to the amount of steam required to obtain the steam to hydrocarbon feedstock weight ratio of the steam cracker feed.

The method for measuring the dew point of a steam cracker feed allows for the measurement of the dew point of a steam cracker feed at a wide range of steam to hydrocarbon weight ratios, also referred to as the steam to oil ratio or STOR.

In another aspect, the invention provides a system for determining the dew point of a vaporised hydrocarbon feedstock, comprising:

a system inlet for receiving gaseous and/or vaporous stream a detector for analyzing the hydrocarbon content in a gaseous and/or vaporous stream having an detector inlet for receiving a gaseous and/or vaporous stream and providing a signal output;

an oven having an internal volume and suitable to maintain the internal volume at a temperature in the range of from 20 to 500° C.;

a first pathway fluidly connecting the system inlet with the detector inlet, wherein at least part of the first pathway is contained in the inner volume of the oven and the first pathway is free from any porous absorbent.

BRIEF DESCRIPTION OF THE DRAWINGS

In FIG. 1 a schematic representation is given of an embodiment of the system according to the invention.

DETAILED DESCRIPTION OF THE INVENTION

The present invention provides a method for determining the dew point of a vaporised hydrocarbon feedstock, also referred to as the first method. Reference herein to the dew point of a vaporised hydrocarbon feedstock is to the hydrocarbon dew point, i.e. the temperature at which the first hydrocarbon components in the vaporised feedstock condense when the fully vaporised hydrocarbon feedstock is cooled. The dew point of a pure hydrocarbon depends on its partial vapour pressure in the hydrocarbon feedstock or mixture of the hydrocarbon feedstock with other compounds such as for instance steam.

In the first method according to the invention the hydrocarbon dew point of a vaporised hydrocarbon feedstock may be determined for a wide range of diluted hydrocarbon feedstocks by providing a hydrocarbon feedstock and a non-hydrocarbonaceous diluent (step (a)) and heating the hydrocarbon feedstock and diluent to a first temperature and maintaining the hydrocarbon feedstock and diluent at the first temperature until all hydrocarbon feedstock is vaporised and a homogeneous mixture of the hydrocarbon feedstock and diluent is obtained (step (b)). The weight ratio of diluent to hydrocarbon feedstock can be chosen freely, although preferably the weight ratio of diluent to hydrocarbon feedstock is in the range of from 0.05 to 100 is used.

The hydrocarbon feedstock and diluent are heated to a first temperature at which all of the hydrocarbon feedstock vaporizes. In case the diluent is provided in a liquid phase, the first temperature is chosen such that also the all of diluent vaporizes. The first temperature is thus a temperature above the dew point of the mixture of the hydrocarbon feedstock and diluent. Preferably, the first temperature is in the range of from 100 to 500° C., more preferably 200 to 450° C.

A first flow of the, now fully vaporized, mixture of hydrocarbon feedstock and diluent is passed through a first zone (step (c)). The first zone is maintained at a second temperature, which is lower than the first temperature. The first flow of the mixture is preferably passed through the first zone through a metal conduit or metal pipe. The first zone may for instance be part or all of the internal volume of an oven encompassing at least part of the metal conduit or metal pipe through which the first flow is passed.

The first flow is allowed to pass through the first zone for a certain time and is subsequently halted (step (d)).

The first flow is replaced by a second flow comprising a non-hydrocarbonaceous sweep gas, and the second flow is passed through the first zone (step (e)). In case the first flow of the mixture was passed through the first zone through a metal conduit or metal pipe, the second flow will be passed through the same metal conduit or metal pipe.

The sweep gas exiting the first zone is provided to a detector suitable for detecting the presence of hydrocarbons. It will be appreciated the residual mixture of hydrocarbons and diluent, which was part of the first flow is first allowed to pass out of the first zone.

Preferably, steps (c) to (e) are repeated one or more times to obtained several analysis results from the detector.

In a next step, i.e. step (f), the temperature of the first zone is decreased. Preferably, the second temperature, i.e. the temperature of the first zone, is decreased in step (f) by in the range of from 0.1 to 10° C., preferably 1 to 5° C. The extent of the decrease of the second temperature may be based on the expected dew point of the hydrocarbons in the mixture. Where small temperature steps are made when the temperature is close to the expected dew point and larger temperature steps where the temperature is expected to be far off the dew point.

In the first method according to the invention, steps (c) to (f) are repeated at least until a hydrocarbon presence is detected in the sweep gas. Preferably, steps (c) to (f) are further repeated at several first zone temperatures below the temperature at which the hydrocarbon presence is detected in the sweep gas. Continuing the measurement below the temperature at which the hydrocarbon presence is first detected in the sweep gas assist in the analysis of the results.

Without wishing to be bound to a particularly theory, it is believed that as long as the second temperature is above the dew point of the hydrocarbons in the mixture, the first flow comprising a fully vaporized mixture will pass through the first zone unchanged and no hydrocarbons will be detected in the sweep gas. However, when the second temperature is below the dew point of at least one of the hydrocarbons in the mixture, a hydrocarbon condensate will be formed in the first zone containing part of the hydrocarbons introduced by the first flow. When subsequently the first flow is replaced by the second flow comprising the sweep gas, the condensed hydrocarbons will re-vaporize due to the reduced or even absent partial vapour pressure of the hydrocarbons in the second flow. The second flow comprising the condensed and re-vaporised hydrocarbons is provided to the detector where the presence of the hydrocarbons is confirmed.

As mentioned above, the first flow is allowed to pass through the first zone for a certain time. This time should be sufficient to, where the temperature is below the dew point, condense an amount of hydrocarbons which is above the detection level of the detector. Preferably, the first flow is allowed to pass through the first zone for in the range of 10 to 3600 seconds.

The second flow comprises a non-hydrocarbonaceous sweep gas. The sweep gas may be any non-hydrocarbonaceous sweep gas. However, where the diluent is a gaseous diluent under the condition existing in the first zone, the sweep gas and diluent are preferably the same. The second flow may be provided separately, however, preferably, the second flow is provided by halting the provision of hydrocarbon feedstock and providing the diluent alone to the first zone.

As the temperature is reduced, the pressure in the first zone may also be reduced. To maintain a constant residence time of the hydrocarbons in first flow of the mixture in the first zone, it is preferred to also provide the first flow exiting first zone to a detector suitable for detecting the presence of hydrocarbons, preferably the same as used for the sweep gas, and controlling the first flow such as to maintain a constant signal output of the detector. Preferably, the first flow is adjusted as it is allowed to flow through the first zone to obtain a desired detector response. When the signal output of the detector is maintained, so will residence time hydrocarbons in the first zone. One preferred way of controlling the first flow is by passing the first flow exiting the first zone through a restrictor inducing a pressure drop downstream of the first zone.

When the first flow is also provided to the detector caution must be taken not to overload the detector. In such as case it is preferred to add a further non-hydrocarbonaceous diluent to the first flow exiting the first zone prior to entering the detector, i.e. downstream of the first zone and upstream of the detector. More preferably, sufficient further diluent is added to maintain the signal output of the detector below 50 wt %, more preferably 15 wt % of the maximum signal output of the detector. Reference to the maximum output signal of the detector is to the signal obtained from the detector when the hydrocarbon concentration in the detector reaches the maximum hydrocarbon concentration that can be analyzed by the detector. The further diluent can be any gaseous non-hydrocarbonaceous diluent, i.e. gaseous at the conditions existing between the first zone and the detector. Preferably, the further diluent is the same as the diluent already comprised in the mixture. The addition of further diluent may also be used to increase the pressure upstream of the point where the further diluent is added.

In one preferred embodiment of the first method according to the invention the first and/or second flow are passed through a Deans switch after exiting the first zone. A Deans switch, which is a commercially available device, is a pneumatically controlled interface system which directs flow from a primary flow direction to a secondary flow direction. Deans switches are well known in the art for the suitability to redirect gaseous flows and do not need any further explication. The Deans switch is activated by a non-hydrocarbonaceous switching gas. The operation of the Deans switch is dependent on the pressure of the gas in primary flow and the pressure applied by the switching gas. Besides providing the ability to divert part or all of the first and/or second flow in an alternative direction, the use of a Deans switch has the particular advantage that by selecting a switching gas pressure which exceeds the pressure of the gas in primary flow passing through the Deans switch, it is possible to allow part of the switch gas to flow into the primary gas flow and thereby act as diluent for the first or second flow. As such the Deans switch may be used to add a further diluent to the first flow exiting the first zone prior to entering the detector, i.e. downstream of the first zone and upstream of the detector. In addition, the use of a Deans switch provides another advantage in that it, by its nature, acts as a restrictor in the first flow inducing a pressure drop downstream of the first zone.

Preferably, the first method according to the invention provides the ability not only to detect the presence of hydrocarbons, but also to analyze the nature of the hydrocarbons in the first and second flow. Therefore is preferred that intermittently a quantity of the first and/or second flow is directed to an analyzer suitable for analyzing the nature of hydrocarbons, preferably a gas chromatography device (GC). This may be done by taking samples of the first and/or second flow and providing these separately to a GC, however, preferably, the method comprises passing the first and/or second flow through a Deans switch after exiting the first zone and operating the Deans switch intermittently to direct part of primary from to a secondary flow, which is provided to a GC.

The first method according to the present invention may be used to determine the dew point of any hydrocarbon feedstock, provided its mixture with the diluent has a dew point below 500° C. Preferably, the hydrocarbon feedstock has a dew point above 175° C., preferably above 200° C., more preferably a dew point in the range of from 175 to 500° C., even more preferably 200 to 450° C.

The dew-point may be determined by for instance plotting the dynamic area fraction, i.e. the fraction of detector area after the first flow is stopped divided by total detector area, obtained from the signal from the first detector versus the temperature. However, any suitable method of analyzing the output signal of the detector may be used.

The non-hydrocarbonaceous diluent may be any diluent that is gaseous at the conditions applied to the first zone and the conditions existing between the first zone and any detector and is inert, i.e. will not react with the hydrocarbons at the temperature and pressure conditions applied. Preferably, the non-hydrocarbonaceous diluent does not contribute to the detector signal, as this would required a correction of the detector signal to correct for the diluents contribution. Preferably, the non-hydrocarbonaceous diluent is a non-hydrocarbonaceous gas, i.e. a diluent that is gaseous at 20° C. and 1 bar absolute, as this will ensure that no diluent will condense at the conditions typically used in the method according to the invention. Preferably, the non-hydrocarbonaceous diluent is nitrogen, helium or argon. The preferences provided herein for the non-hydrocarbonaceous diluent apply mutates mutandis for the sweep gas, further non-hydrocarbonaceous diluent and Deans switch gas.

The first method may be used to determine the dew point of a vaporised hydrocarbon feedstock in a wide pressure range. Preferably, at pressures in the range of from 1 to 20 bar (absolute), more preferably 1 to 10 bar (absolute). Preferably, the any apparatus used to work the first method is the pre-pressurised to the pressure at which the first method is to be worked.

As mentioned herein above, a suitable application of the first method according to the inventions is in the measurement of the dew point of steam cracker feeds. Steam cracker feeds typically comprise steam and a hydrocarbon feedstock at a pre-determined steam to hydrocarbon feedstock weight ratio or STOR. One feature determining in the selection of the STOR is the need to prevent condensation of the hydrocarbons in the steam cracker feedstock in specific parts of the steam cracking process.

Therefore in a further aspect the present invention also provides for a method for estimating the dew point of a steam cracker feed comprising steam and a hydrocarbon feedstock at a steam to hydrocarbon feedstock weight ratio. The method is further referred to as the second method. In the second method according to the invention, an amount of the hydrocarbon feedstock is provided together with an amount of diluent other than steam. The amount of the diluent is equimolar to the amount of steam required to obtain the steam to hydrocarbon feedstock weight ratio of the steam cracker feed. Thus for a steam cracker feed having a STOR of 1, a 1 kg sample of hydrocarbon feedstock would be provided together with 4/18 kg (0.22 kg) of He (molar mass 4 g) as diluent or with 18/18 kg (1 kg) of Ar (molar mass 18).

The provided hydrocarbon feedstock and diluent are subsequently analysed using the first method for determining the dew point of a hydrocarbon feedstock according to the invention.

In another aspect, the invention provides a system for determining the dew point of a vaporised hydrocarbon feedstock using the first and/or second method according to the invention. The system according to the invention will be described in more detail with reference to FIG. 1.

The system (1) for determining the dew point of a hydrocarbon feedstock comprises:

(i) a system inlet (5) for receiving gaseous and/or vaporous stream, wherein the term vaporous stream refers to a stream comprising components which were vaporised prior to being provided to the system inlet.

(ii) a detector (10) for analyzing the hydrocarbon content in a gaseous and/or vaporous stream having a detector inlet (15) for receiving a gaseous and/or vaporous stream and providing a signal output. Reference herein to a signal output is to any electrical, numerical or visual output representing the analysis provided by the detector. Any detector suitable for analyzing the hydrocarbon content in a gaseous and/or vaporous stream may be used. One preferred detector is a Flame Ionization detector (FID).

(iii) an oven (20) having an internal volume (25) and suitable to maintain the internal volume at a temperature in the range of from 20 to 500° C.;

(iv) a first pathway (30) fluidly connecting the system inlet (5) with the detector inlet (15), wherein at least part, and preferably all, of the first pathway (30) is contained in the inner volume of the oven. The advantage of having all of the first pathway contained in the inner volume is that the whole first pathway is exposed to the same conditions, preventing any undesired temperature effects as the first pathway exits the inner volume of the oven and thus the need to take any additional measure to prevent these temperature effects of occurring. The first zone (32), i.e. the part of internal volume (25) left of dotted line (32a), according the first and second method of the invention is also comprised in the inner volume of the oven. The first pathway is free from any porous absorbent as such an absorbent may influence the condensation and re-vaporization behaviour of the hydrocarbons in the hydrocarbon feedstock. The first pathway is preferably provided in the form of one or more metal conduit, metal tubes or metal piping.

Preferably, the system further comprises a second detector (35) for analyzing the nature of a hydrocarbon compound having a detector inlet (40) and providing a signal output. Any detector suitable for analyzing the nature of a hydrocarbon compound may be used, however, preferably a GC or a combination of a GC with a Mass Spectrometer is used (GC/MS). A Deans switch (45) located in the first pathway (30) and suitable to divert a gaseous and/or vaporous stream from the first pathway to a second pathway (50) is preferably provided. Preferably, the second pathway (50) fluidly connects the Deans switch to the detector inlet of the second detector. The Deans switch may be operated by switch gas provided via a conduit (47a and 47 b) and may be controlled by a valve (47c).

Preferably, the system further comprises an evaporator (55), suitable for evaporating liquids in a temperature range of from 100 to 500° C., and having one or more inlets (60) for receiving diluent and liquid hydrocarbon and an outlet (65) fluidly connected to the system inlet (5). The evaporator may be located externally, but is preferably provided in the inner volume of the oven. When the evaporator is located inside the internal volume of the oven, the evaporator inner volume does not form part of the first zone and may be controlled at a temperature above that of the first zone to ensure full evaporation of the hydrocarbon feedstock. In case, the volume of hydrocarbon feedstock and diluent provided to the evaporator is exceeding the capacity of the system, a further evaporator outlet may be provided to purge part of the evaporated hydrocarbon feedstock and diluent mixture.

Preferably, a quick-swap (70) is provided in the first, and optionally to the second, pathway. The quick-swap (70) may be set and used to increase the pressure in the first, and optionally to the second, pathway by addition of a further gaseous diluent. Typically, such a quick-swap (70) comprises one inlet fluidly connected to the first pathway (30), one inlet for providing further diluent and an outlet fluidly connected to the detector (10) for analyzing the hydrocarbon content in a gaseous and/or vaporous stream. The quick-swap may be controlled using an electronic pressure controller (EPC) (75), which is fluidly connected to the inlet for further diluent.

To assist in the interpretation of the output of the detectors, such as a FID or GC, it is preferred that the system further includes a computer comprising a software system for data acquisition and analysis. This computer is connected to any one or more of the detectors in a way that the output of the detector is relayed to the computer.

EXAMPLES

The invention is illustrated by the following non-limiting examples.

To show the ability of the method according the present invention to determine the dew-point of a mixture of hydrocarbons and a diluent, the dew point of two model hydrocarbons (HC), i.e. n-decane and n-hexadecane, was determined at various extents of dilution with Argon. The experimental conditions are provided in Table 1. In Table 2 the dew-point as determined with the methods according to the present invention is compared to the literature dew point. It will be clear from Table 2, that the method according the present invention is very suitable for determining the dew point of diluted vaporised hydrocarbons.

TABLE 1

| Pressure kPa gauge | HC flow µl/min | Ar flow Nml/min | STOR* — | HC flow ×10$^{-5}$ mol | Ar flow ×10$^{-4}$ mol | Mol fraction HC — | Total Pressure mbar absolute | Partial pressure HC mbar absolute |
|---|---|---|---|---|---|---|---|---|
| n-decane ||||||||||
| 250 | 11.85 | 6.0 | 0.51 | 6.09 | 2.46 | 0.20 | 3389 | 673.8 |
| 150 | 11.85 | 4.0 | 0.34 | 6.09 | 1.64 | 0.27 | 2389 | 648.0 |
| 150 | 11.85 | 6.0 | 0.51 | 6.09 | 2.45 | 0.20 | 2389 | 475.1 |
| 150 | 11.85 | 8.0 | 0.68 | 6.09 | 3.27 | 0.16 | 2389 | 374.9 |
| 150 | 11.85 | 12.0 | 1.02 | 6.09 | 4.91 | 0.11 | 2389 | 263.9 |
| 150 | 11.85 | 20.0 | 1.70 | 6.09 | 8.18 | 0.07 | 2389 | 165.7 |
| n-hexadecane ||||||||||
| 350 | 11.85 | 6.0 | 0.49 | 6.09 | 2.47 | 0.14 | 4389 | 618.4 |
| 350 | 11.85 | 12.1 | 0.97 | 6.09 | 4.93 | 0.08 | 4389 | 333.7 |

*Theoretical, based on an equimolar amount of water replacing the Argon diluent

TABLE 2

| Measured dew point ° C. | Literature dew point ° C. |
|---|---|
| n-decane | |
| 158.4 | 159.0 |
| 157.2 | 157.5 |
| 146.7 | 146.8 |
| 138.3 | 139.0 |
| 129.0 | 128.0 |
| 114.8 | 114.6 |
| n-hexadecane | |
| 263.3 | 265.0 |
| 240.2 | 241.0 |

What is claimed is:

1. A method for determining the dew point of a vaporised hydrocarbon feedstock, comprising
    a) providing a hydrocarbon feedstock and a non-hydrocarbonaceous diluent;
    b) heating the hydrocarbon feedstock and diluent to a first temperature and maintaining the hydrocarbon feedstock and diluent at the first temperature until all hydrocarbon feedstock is vaporized and a homogeneous mixture of the hydrocarbon feedstock and diluent is obtained;
    c) passing a first flow of the mixture through a first zone maintained at a second temperature, which is lower than the first temperature;
    d) halting the first flow;
    e) passing a second flow comprising a non-hydrocarbonaceous sweep gas through the first zone and providing the sweep gas exiting the first zone to a detector suitable for detecting the presence of hydrocarbons;
    f) decreasing the temperature of the first zone,
        wherein steps (c) to (f) are repeated at least until a hydrocarbon presence is detected in the sweep gas.

2. A method according to claim 1, wherein the hydrocarbon feedstock has a dew point above 175° C.

3. A method according to claim 1, wherein the second temperature is decreased in step (f) by in the range of from 0.1 to 10° C.

4. A method according to claim 1, wherein steps (c) to (e) are repeated one or more times prior to decreasing the temperature in step (f).

5. A method according to claim 1, wherein the first temperature is in the range of from 100 to 500° C.

6. A method according to claim 1, wherein the first flow exiting the first zone is provided to a detector suitable for detecting the presence of hydrocarbons and the first flow is controlled to maintain a constant signal output of the detector, thereby maintaining a constant hydrocarbon residence time in the first zone.

7. A method according to claim 6, wherein the first flow is controlled by passing the first flow exiting the first zone through a restrictor inducing a pressure drop.

8. A method according to claim 1, wherein the first flow exiting the first zone is provided to the detector suitable for detecting the presence of hydrocarbons and a further non-hydrocarbonaceous diluent is added to the first flow exiting the first zone prior to entering the detector.

9. A method according to claim 1, wherein the non-hydrocarbonaceous diluent is a non-hydrocarbonaceous gas.

10. A method for measuring the dew point of a steam cracker feed comprising steam and a hydrocarbon feedstock at a steam to hydrocarbon feedstock weight ratio, comprising providing an amount of the hydrocarbon feedstock and an amount of non-hydrocarbonaceous diluent other than steam; and
    determining the dew point of the vaporised hydrocarbon feedstock with a method according to claim 1,
    wherein the amount of diluent provided is equimolar to the amount of steam required to obtain the steam to hydrocarbon feedstock weight ratio of the steam cracker feed.

11. A system for determining the dew point of a vaporised hydrocarbon feedstock, comprising:
    a system inlet for receiving gaseous and/or vaporous stream
    a detector for analyzing the hydrocarbon content in a gaseous and/or vaporous stream having an detector inlet for receiving a gaseous and/or vaporous stream and providing a signal output;
    an oven having an internal volume and suitable to maintain the internal volume at a temperature in the range of from 20 to 500° C.;
    a first pathway fluidly connecting the system inlet with the detector inlet, wherein at least part of the first pathway is contained in the inner volume of the oven and the first pathway is free from any porous absorbent,
    wherein the system further comprises an evaporator, suitable for evaporating liquids in a temperature range of from 100 to 500° C., having one or more inlets for receiving diluent and liquid hydrocarbon and an outlet fluidly connected to the system inlet.

12. A system according to claim 11, wherein the system further comprises:
    a second detector for analyzing the nature of a hydrocarbon compound having a detector inlet and providing a signal output; and
    a Deans switch located in the first pathway suitable to divert a gaseous and/or vaporous stream from the first pathway to a second pathway fluidly connecting the Deans switch to the detector inlet of the second detector.

13. A system according to claim 11 wherein the evaporator is contained in the inner volume of the oven.

14. A system according to claim 11, wherein a quick-swap is provided in the first pathway, set to increase the pressure in the first pathway by addition of a gaseous diluent.

* * * * *